(12) United States Patent
Bourne et al.

(10) Patent No.: US 10,537,471 B2
(45) Date of Patent: Jan. 21, 2020

(54) HYDRAULIC PUMP FOR OPHTHALMIC SURGERY

(71) Applicant: Novartis AG, Basel (CH)

(72) Inventors: John Morgan Bourne, Irvine, CA (US); Gary P. Sorensen, Laguna Niguel, CA (US)

(73) Assignee: Novartis AG, Basel (CH)

( * ) Notice: Subject to any disclaimer, the term of this patent is extended or adjusted under 35 U.S.C. 154(b) by 733 days.

(21) Appl. No.: 14/471,089

(22) Filed: Aug. 28, 2014

(65) Prior Publication Data

US 2015/0297405 A1 Oct. 22, 2015

Related U.S. Application Data

(60) Provisional application No. 61/981,012, filed on Apr. 17, 2014.

(51) Int. Cl.
*A61F 9/007* (2006.01)
*A61M 1/00* (2006.01)
(Continued)

(52) U.S. Cl.
CPC ....... *A61F 9/00736* (2013.01); *A61M 1/0058* (2013.01); *A61M 1/0064* (2013.01);
(Continued)

(58) Field of Classification Search
CPC .................. A61F 9/00736; A61F 9/007; A61F 2210/0612; A61F 2205/12; A61F 1/0035;
(Continued)

(56) References Cited

U.S. PATENT DOCUMENTS 4,405,289 A 9/1983 Nakashima
4,790,726 A 12/1988 Balkau et al.
(Continued)

FOREIGN PATENT DOCUMENTS

EP 0450267 A2 10/1991
EP 2365220 A1 9/2011
(Continued)

OTHER PUBLICATIONS

International Search Report and Written Opinion of the International Searching Authority, International Application No. PCT/2015/026293, dated Jul. 23, 2015, 10 pages.

*Primary Examiner* — Devon C Kramer
*Assistant Examiner* — Christopher J Brunjes

(57) ABSTRACT

Apparatuses, systems, and method for hydraulic pumps are disclosed. Particularly, hydraulic pumps for ophthalmic surgical procedures are disclosed. Hydraulic pumps within the scope of the disclosure may include an aspiration pump. An example aspiration pump may include first and second hydraulic cylinders and a plurality of one-way valves that are operable to permit fluid flow into a first part of a hydraulic cylinder responsive to movement of a piston within the hydraulic cylinder in a first direction and operable to permit fluid to flow out of the hydraulic cylinder responsive to movement of the piston in a second direction opposite the first direction. The aspiration pump may be attached to a housing of a hand piece, or a portion of the aspiration pump may be received into the housing of the hand piece.

2 Claims, 8 Drawing Sheets

(51) Int. Cl.
  *F04B 9/10*     (2006.01)
  *F04B 9/117*    (2006.01)
(52) U.S. Cl.
  CPC .............. *A61M 1/0068* (2014.02); *F04B 9/10*
      (2013.01); *F04B 9/1176* (2013.01); *A61M*
      *1/0035* (2014.02); *A61M 1/0043* (2013.01);
      *A61M 2210/0612* (2013.01)
(58) Field of Classification Search
  CPC .... A61F 1/0043; A61F 1/0058; A61F 1/0064;
      A61F 1/0068; F04B 15/02; F04B 49/06;
      F04B 39/08; F04B 5/02; F04B 9/109;
      F04B 9/103; F04B 9/12; F04B 9/105;
      F04B 9/1172; F04B 9/1176; F04B 9/10;
      A61M 1/0058; A61M 1/0062; A61M
      1/0064; A61M 1/0068; A61M 1/0023;
      A61M 1/0035; A61M 1/0039; A61M
      1/0043
  USPC .......................................... 604/118, 119, 153
  See application file for complete search history.

(56) References Cited

U.S. PATENT DOCUMENTS

| | | | |
|---|---|---|---|
| 4,854,825 A | 8/1989 | Bez et al. | |
| 5,038,965 A | 8/1991 | Cater | |
| 5,213,478 A * | 5/1993 | Hoya | F04B 9/1178 417/342 |
| 5,267,956 A | 12/1993 | Beuchat et al. | |
| 5,364,342 A | 11/1994 | Beuchat et al. | |
| 5,443,370 A | 8/1995 | Wang | |
| 5,529,463 A * | 6/1996 | Layer | F04B 1/02 128/DIG. 12 |
| 5,562,692 A * | 10/1996 | Bair | A61B 17/3203 604/22 |
| 6,206,658 B1 * | 3/2001 | Nishioka | B01J 3/006 210/603 |
| 2002/0049461 A1 * | 4/2002 | Kanda | A61F 9/00763 606/167 |
| 2002/0106292 A1 * | 8/2002 | Chowaniec | F02C 7/1435 417/403 |
| 2005/0234394 A1 | 10/2005 | Ross | |
| 2008/0281254 A1 * | 11/2008 | Humayun | A61F 9/00736 604/22 |
| 2010/0249693 A1 * | 9/2010 | Links | A61F 9/00736 604/22 |
| 2011/0054385 A1 * | 3/2011 | Eichler | A61M 1/0058 604/22 |
| 2012/0089080 A1 | 4/2012 | Ross et al. | |
| 2012/0294742 A1 * | 11/2012 | Reich | F04B 43/1292 417/474 |
| 2012/0301328 A1 * | 11/2012 | Adler | F04B 3/00 417/246 |
| 2013/0150782 A1 * | 6/2013 | Sorensen | A61M 3/0283 604/30 |
| 2014/0224829 A1 * | 8/2014 | Capone | F04B 49/06 222/23 |
| 2014/0296892 A1 * | 10/2014 | Uchida | B05B 5/16 606/167 |
| 2016/0222985 A1 * | 8/2016 | Oklejas, Jr. | F04B 53/14 |

FOREIGN PATENT DOCUMENTS

| | | |
|---|---|---|
| JP | S57-157076 A | 9/1982 |
| JP | H8-505065 A | 6/1996 |

* cited by examiner

HYDRAULIC PUMP FOR OPHTHALMIC SURGERY

CROSS REFERENCE TO RELATED APPLICATIONS

This application claims the benefit of U.S. Provisional Application No. 61/981,012 filed Apr. 17, 2014, the contents of both being incorporated herein by reference.

TECHNICAL FIELD

The present disclosure relates to systems, apparatuses, and methods for aspirating materials through a hand piece and, particularly, to systems, apparatuses, and methods directed to a providing pumping at a hand piece to generate an aspiration fluid flow.

BACKGROUND

Aspiration of fluid may be needed in any number of surgical procedures. For example, in the area of ophthalmology, aspiration of materials may be needed in numerous types of surgical procedures. Aspiration is used in vitreoretinal surgical procedures as well as phacoemulsification surgical procedures. During the course of a phacoemulsification procedure, lens fragments may be removed via an aspiration fluid flow. The fluid flow may be generated by a surgical console and communicated to the eye through a hand piece.

SUMMARY

According to one aspect, the disclosure describes a pump system that may include an aspiration pump and a plurality of one-way valves. The aspiration pump may include a first cylinder and a second cylinder. The first cylinder may include a first piston moveable within the first cylinder. The first piston divides the first cylinder into a first portion and a second portion. A first opening may be formed at a first end of the first cylinder, and a second opening may be formed at the first end of the first cylinder. A first one-way valve may be in fluid communication with the first portion of the first cylinder via the first opening. The first one-way valve is operable to permit fluid flow into the first portion of the first cylinder when the first piston is displaced in a first direction. A second one-way valve may be in fluid communication with the first portion of the first cylinder via the second opening. The second one-way valve is operable to permit fluid flow out of the first portion of the first cylinder when the first piston is displaced in a second direction opposite the first direction. A third one-way valve may be in fluid communication with the first portion of the second cylinder via the third opening. The third one-way valve is operable to permit fluid flow into the first portion of the second cylinder when the second piston is displaced in the first direction. A fourth one-way valve may be in fluid communication with the first portion of the second cylinder via the fourth opening. The fourth one-way valve is operable to permit fluid flow out of the second cylinder when the second piston is displaced in the second direction.

Another aspect of the disclosure encompasses a pump system that includes a first fluid circuit and a second fluid circuit. Each of the first fluid circuit and the second fluid circuit may include a first cylinder, a second cylinder, and a fluid conduit extending between the first cylinder and the second cylinder. The first cylinder includes a first piston that divides an interior chamber of the first cylinder into a first portion and a second portion. The first piston is moveable in the first cylinder in a first direction and a second direction opposite the first direction. The second cylinder includes a second piston that divides an interior chamber of the second into a first portion and a second portion. The second piston is moveable in the second cylinder in the first direction and the second direction. The fluid conduit, the second portion of the first cylinder, and the first portion of the second cylinder are in fluid communication with each other. A fluid may be contained in the second portion of the first cylinder, the first portion of the second cylinder, and the fluid conduit.

Each of the first fluid circuit and the second fluid circuit may also include a first one-way valve and a second one-way valve. The first one-way valve provides selective communication with the first portion of the first cylinder. The first one-way valve may be moveable into an open configuration when the first piston is displaced in the first direction and moveable into a closed configuration when the first piston is moveable in the second direction. The second one-way valve provides selective communication with the first portion of the first cylinder. The second one-way valve may be moveable into a closed configuration when the first piston is displaced in the first direction and moveable into an open configuration when the piston is displaced in the second direction.

The various aspects may include one or more of the following features. The aspiration pump may also include a conduit in fluid communication with the second one-way valve and the fourth one-way valve. The conduit may be adapted to conduct fluid expelled from the first cylinder and second cylinder through the second one-way valve and fourth one-way valve, respectively. The aspiration pump may also include a collection container in fluid communication with the conduit. Fluid expelled from the first cylinder and the second cylinder may be received in the collection container. The pump system may also include a pump actuator. The pump actuator may be operable to displace the first piston in the first cylinder and the second piston in the second cylinder.

The pump actuator may include a third cylinder. A third piston may be disposed in the third cylinder and divide the third cylinder into a first portion and a second portion. The first portion of the third cylinder may be in fluid communication with the second portion of the first cylinder. The pump actuator may also include a fourth cylinder. A fourth piston may be disposed in the fourth cylinder and divide the fourth cylinder into a first portion and a second portion. The first portion of the fourth cylinder may be in fluid communication with the second portion of the second cylinder. A liquid may be fluidly communicated between the first portion of the third cylinder and the second portion of the first cylinder and between the first portion of the fourth cylinder and the second portion of the second cylinder. Displacement of the third piston within the third cylinder correspondingly displaces the first piston in the first cylinder. Displacement of the fourth piston within the fourth cylinder correspondingly displaces the second piston in the second cylinder.

A first actuator may be coupled to the third piston and moveable in a first longitudinal direction and a second longitudinal direction. A second actuator may be coupled to the third piston and moveable in the first longitudinal direction and the second longitudinal direction. Movement of the first actuator in either the first longitudinal direction or the second longitudinal correspondingly displaces the first piston in the first direction or the second direction, respectively. Movement of the second actuator in either the first longitudinal direction or the second longitudinal direction correspondingly displaces the second piston in the first direction or the second direction, respectively.

A pump actuator may include a fluid conduit network in communication with the second portion of the first cylinder and the second portion of the second cylinder; a pump in fluid communication with the fluid communication with the fluid conduit network; and a plurality of valves disposed in the fluid conduit network. The pump is operable to pump fluid through the fluid conduit network. The plurality of valves are moveable between a first position in which the first piston is displaced in the first direction and the second piston is displaced in the second direction and a second position in which the first piston is displaced in the second direction and the second piston is displaced in the first direction. The pump actuator may be receivable into a cassette receiving portion of a surgical console. The aspiration pump may be detachably coupleable to an aspirating hand piece.

The various aspects may also include one or more of the following features. A collection container may also be included. An outlet of each of the second one-way valves may be in fluid communication with the collection container. A first actuator and a second actuator may also be included. Each of the first actuator and second actuator may be moveable in a first longitudinal direction and a second longitudinal direction opposite the first longitudinal direction. The first actuator may be coupled to the second piston of the first fluid circuit, and the second actuator may be coupled to the second piston of the second fluid circuit. Displacement of the first actuator in the first longitudinal direction and the second longitudinal direction causes displacement of the first piston of the first fluid circuit in the first direction and second direction, respectively. Displacement of the second actuator in the first longitudinal direction and the second longitudinal direction causes displacement of the first piston of the second fluid circuit in the first direction and the second direction, respectively. The first actuator may be coupled to the second piston of the first fluid circuit, and the second actuator may be coupled to the second piston of the second fluid circuit. A controller may be included and adapted to reciprocate the first piston and the second piston of the first fluid circuit out of phase with the first piston and the second piston of the second fluid circuit. The first cylinder of the first fluid circuit and the first cylinder of the second fluid circuit may be coupleable to a surgical hand piece. The first cylinder of the first fluid circuit and the first cylinder of the second fluid circuit may be configured to directly attach to portion of a surgical hand piece. The liquid may be a saline solution.

According to another aspect, a pump system may include a first cylinder and a pump actuator. The first cylinder may include a first piston moveable within the first cylinder in response to a change in pressure acting on the piston. The first piston may divide the first cylinder into a first portion and a second portion. A fluid inlet may be formed in the first portion in fluid communication with an aspiration line, and a fluid outlet may be formed in the first portion in fluid communication with a fluid discharge line. The pump actuator may include a second cylinder. The second cylinder may include a second piston moveable within the second cylinder in response to a force applied thereto. The second piston may divide the second cylinder into a first portion and a second portion. The first portion of the second cylinder may be in fluid communication with the second portion of the first cylinder. A first one-way valve may be in fluid communication with the fluid inlet. The first one-way valve may be configured to permit fluid flow into the first portion of the first cylinder. A second one-way valve may be in fluid communication with the fluid outlet. The second one-way valve may be configured to permit fluid flow out of the first portion of the first cylinder.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

The present disclosure is directed to systems, methods, and apparatuses for generating a fluid flow. More particularly, the present disclosure describes systems, methods, and apparatuses directed to a pump operable to generate an aspiration fluid flow during a surgical procedures. Still further, the disclosure describes example aspiration pumps integrated with a surgical hand piece. In some instances, the pumps are disposable after a single use. In other instances, the example pumps may be reusable. Although the description may reference ophthalmic surgical procedures, the scope of the disclosure is not so limited. Rather, the present disclosure is intended to encompass any applicable uses.

Figure 7:
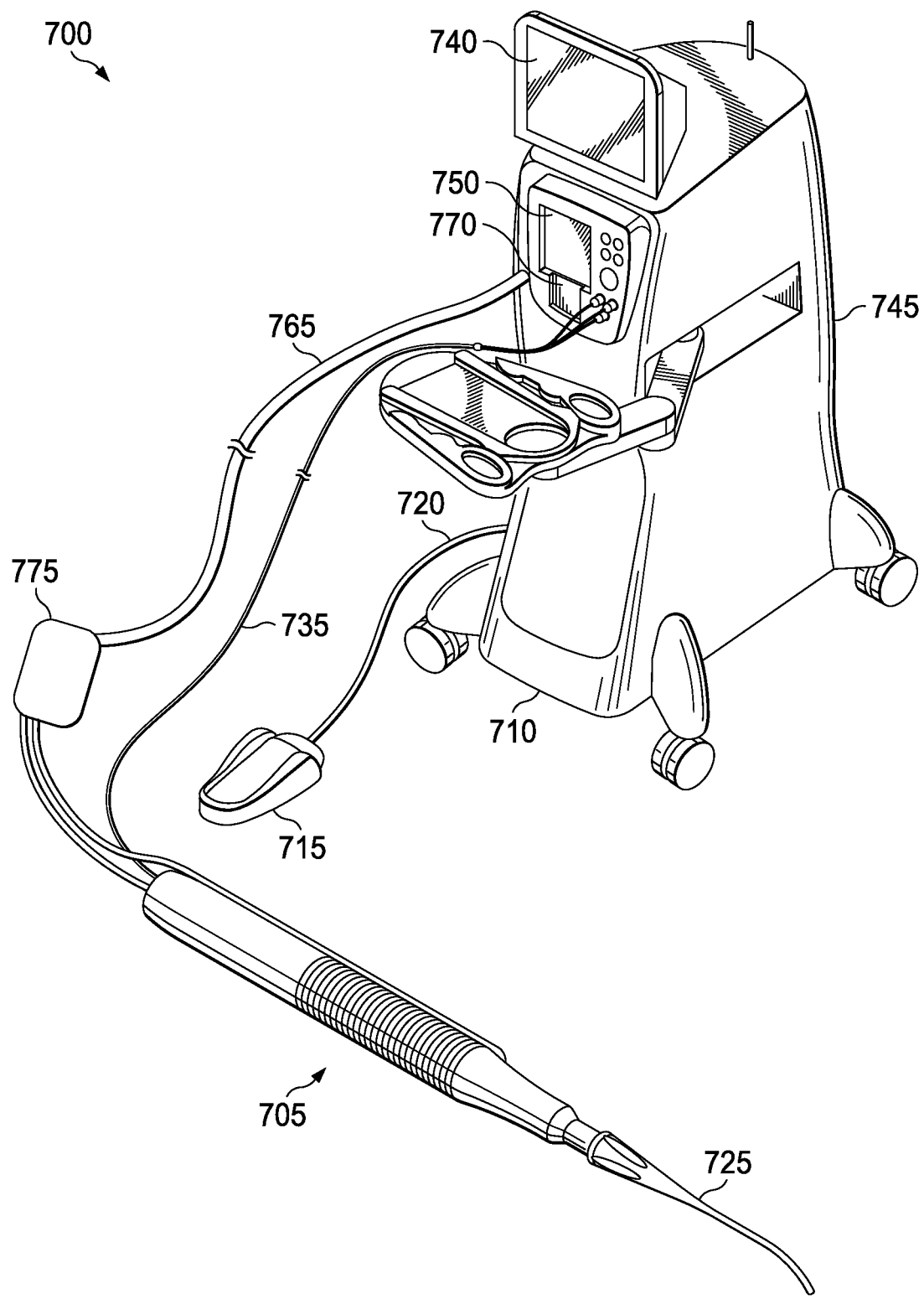
FIG. 7 shows an example ophthalmic surgical system incorporating the principles described herein.

FIG. 7 shows an example ophthalmic surgical system 700. Though the surgical system 700 shown in FIG. 7 is an ophthalmic surgical system, the surgical system 700 may be any surgical system, including a system for performing otic, nasal, throat, maxillofacial, or other surgeries. The system 700 is operable to provide electrical power, which may be used to generate ultrasonic power, and pressurized irrigation fluid to a hand piece 705. In some implementations, the hand piece 705 may be a phacoemulsification hand piece.

In the illustrated embodiment, the system 700 includes a surgical console 710, the hand piece 705, and a footswitch 715 connected to the surgical console 710 via a bi-directional bus or cable 720. An instrument tip 725 for treating a patient condition is attached to the hand-piece 705. In some instances, the instrument tip 725 may be arranged to invasively penetrate a patient's eye. The hand piece 705 is connected to the surgical console 710 through a pump system 765. In some instances, a portion of the pump system 765 includes a segment 770 that couples to the console 710 and a segment 775 that couples to the hand piece 705. In some instances, all or a portion of the pump system 765 is disposable. A footswitch 715 may be used to control the pump system 765. The footswitch 115 is connected to the surgical console 710 though a cable 720. In some implementations, power is supplied to the hand piece 705 through an electrical cable 735 extending from the surgical console 710.

The surgical console 710 also includes a graphic user interface 740 connected to a body 745 and a control console 750 disposed on a surface of the body 745. In some implementations, the graphic user interface 740 may include a liquid crystal display (LCD) with touch screen capability. In other implementations, the graphic user interface 740 may include any of a variety of display devices, including for example, LED displays, CRT's, and flat panel screens. The graphic user interface 740 may include additional input devices or systems, including for example, a keyboard, a mouse, a joystick, dials, and buttons, among other input devices.

The system 700 may include a microprocessor, random access memory (RAM), read only memory (ROM), input/output circuitry such as the bus 720, an audio output device, and other components of microsurgical systems known to those in the art. These may be carried on or may form a part of the console 710, or may be disposed elsewhere about the system 700. The microprocessor may be operable to control various aspects of the surgical system 700. For example, the microprocessor may form at least part of a controller operable to control actuation of the pump systems described herein. A variety of peripheral devices may also be coupled to the system 700, such as storage devices (hard disk drive, CD ROM drive, etc.), printers, and other input/output devices.

The pump system 765 embodying principles described herein is discussed in the context of a phacoemulsification tool. However, the scope of the disclosure is not so limited. Rather, the pump system 765 may be used with other types of surgical instruments in other types of surgical procedures. Thus, other surgical procedures, including other ophthalmic surgical procedures, may also utilize the pump systems described herein.

Figure 1:
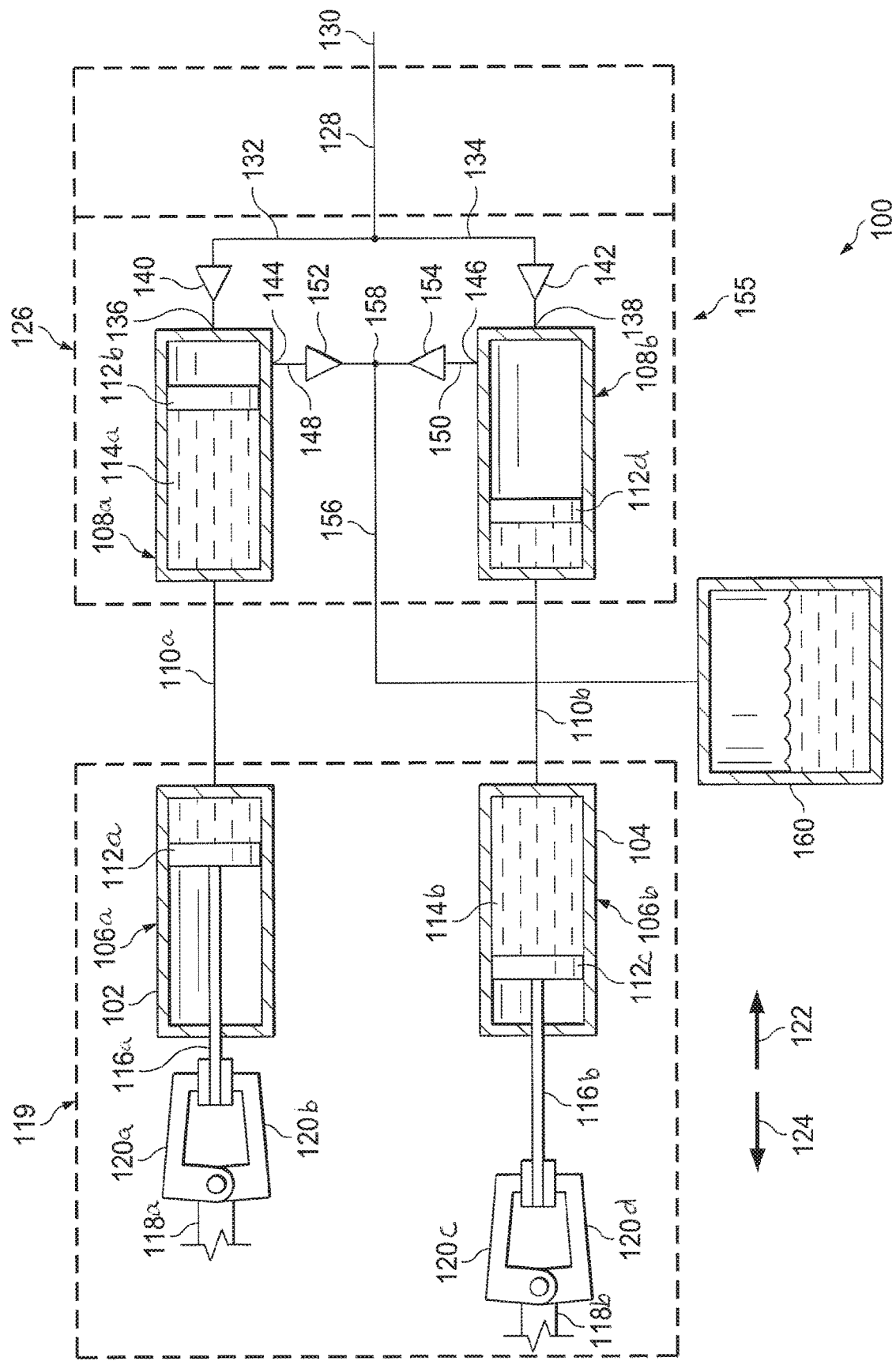
FIG. 1 is a schematic illustration of an example hydraulic pump operable to generate an aspiration fluid flow.

FIG. 1 shows an example pump system 100. The system 100 includes a first fluid circuit 102 and a second fluid circuit 104. Although only two fluid circuits are illustrated, the scope of the disclosure is not so limited. Rather, other implementations may have additional or fewer fluid circuits. For example, in some implementations, a single fluid circuit may be used. In other implementations, more than two fluid circuits may be used. Also, for example, for implementations including multiple fluid circuits, one or more of the fluid circuits may operate (as described in more detail below) out of phase with the one or more different fluid circuits to substantially decreases or eliminate pulsations in the generated aspiration fluid flow.

Each of the first fluid circuit 102 and the second fluid circuit 104 may include a cylinder 106 (106a and 106b, respectively), a cylinder 108 (108a and 108b, respectively), and a conduit 110 (110a and 110b, respectively) that provides fluid communication between the respective cylinders 106a and 108a and cylinders 106b and 108b. Each of the cylinders 106a, b and cylinders 108a, b includes a piston 112a, b, c, and d, respectively, disposed and moveable therein. The first fluid circuit 102 and the second fluid circuit 104 may include a hydraulic fluid 114a, b, respectively, disposed between respective pistons 112a and b and pistons 112c and d.

In some implementations, the hydraulic fluid 114a, b completely fills the volume extending between the pistons 112a, b and 112c, d of the respective fluid circuit 102, 104. Pistons 112a, b, c, and d divide their respective cylinders into two compartments and provide a seal therebetween. Movement of the pistons 112a, b, c, and d within their respective cylinders alters a volume of the two compartments such that an increase in one compartment results in a decrease in the other compartment by the same amount.

The conduits 110a, b may be a length of flexible tubing. For example, the conduits 110a, b may be a length of vacuum and pressure tubing. In some instances, tubing forming the conduits 110a, b may have a wall thickness that provides enough strength and/or rigidity to prevent or restrict volume fluctuations in the tubing lumen, while still providing a sufficient amount of flexibility for a user (e.g., a surgeon or other medical professional) to easily manipulate an instrument or hand piece coupled to the conduits 110a, b, such as during a procedure. In some instances, the conduits 110a, b may be approximately six feet in length. Such a length may provide a user with enough slack to comfortably manipulate an instrument or hand piece attached thereto during a procedure. However, the scope of the disclosure is not so limited. Rather, other lengths for the conduits 110a, b are also contemplated. For example, the conduits 110a, b may have a length less than twelve feet. In other instances, the conduits 110a, b may have a length within a range of about four to eight feet. However, the length of conduits 110a, b may be any desired length.

In some implementations, a connecting member 116a is coupled to and extends from the piston 112a of the cylinder 106a, and a connecting member 116b is coupled to and extends from the piston 112c of the cylinder 106b. The system 100 may also include actuators 118a, b operable to selectively grip the connecting members 116a, b, respectively. For example, the actuator 118a may include grasping members 120a, b that are moveable between an engaged configuration in which the grasping members 120a, b grip the connecting member 116a and a disengaged configuration in which the grasping members 120a, b are disengaged from the connecting member 116a. Similarly, the actuator 118b includes grasping members 120c, d that are movable between an engaged configuration in which the grasping members 120c, d grip he connecting member 116b and a disengaged configuration in which the grasping members 120c, d are disengaged from the connecting member 116b. In FIG. 1, the actuators 118a, b are shown in an engaged configuration. The actuators 118a, b are also operable to oscillate in the directions of arrows 122 and 124.

The grasping members 120a, b and 120c, d may be disengaged from the respective connecting members 116a, b in order to cease pumping of the system 100 quickly. Cessation of pumping may be desired, for example, to quickly relieve any residual vacuum in aspiration line 128, discussed in more detail below. For example, it may be desirable to stop pumping immediately in response to an occlusion within a hand piece, such as hand piece 126 discussed below, or the system 100. This may avoid or reduce the incidence of post-occlusion surge. By releasing the connecting members 116a, b, rather than merely stopping movement of the actuators 118a, b, any remaining force on the actuators 118a, b is not transferred to the system 100 and residual pressure differentials in the system are immediately relieved.

The actuators 118a, b may be used to operate the first and second fluid circuits 102, 104. For example, the actuators 118a, b may be actuated into the engaged configuration to engage the connecting members 116a, b, respectively, and oscillated in the direction of arrows 122, 124. In response to the oscillating movement of the actuators 118a, b, the pistons 112a, c of cylinders 106a, b, respectively, are displaced. The force asserted by the pistons 112a, c of cylinders 106a, b, respectively, is imparted to the pistons 112b, c of the cylinders 108b, b by the hydraulic fluid 114a, b, respectively.

Particularly, as a connecting member 116a or 116b is displaced in the direction of arrow 124, the respective piston 112a or 112c is also displaced in the direction of arrow 124, causing a portion of the cylinder 106a or 106b filled with the hydraulic fluid 114a or 114b to increase. In turn, as a result of fluid continuity, hydraulic fluid 114a or 114b in the respective cylinder 108a or 108b is evacuated into the associated conduit 110a or 110b causing the piston 112b or 112d in respective cylinder 108a or 108b to be displaced in the direction of arrow 124. As a result, a volume of a portion of the cylinder 108a or 108b on an opposite side of the associated piston 112b or 112d increases, generating a vacuum which operates to draw aspirated materials into cylinder 108. In a similar manner, displacement of the connecting members 116a, b and associated pistons 112a c of respective cylinders 106a, b in the direction of arrow 122 results in aspirated material in cylinders 108a, b being expelled therefrom. Consequently, the pistons 112b d of cylinders 108a, b are displaced in the same direction as respective pistons 112a c of cylinders 106a, b. Thus, pistons 112b d of respective cylinders 108a, 108b are hydraulically actuated as a result of displacement of corresponding pistons 112a c of respective cylinders 106a b.

Although the example system 100 shown in FIG. 1 includes actuators 118a, b that have grasping members 120a, b and 120c, d, respectively, that are moveable between an engaged configuration and a disengaged configuration, other implementations may include actuators that are fixedly engaged to the connecting members 116a, b. That is, in some instances, the system 100 may include actuators that do not disengage from the connecting members 116a, b.

In still other implementations, the actuators 118a, b may be eliminated altogether. For example, in some implementations, the pistons 112 a, c in cylinders 106a, b, respectively, may be actuated by pneumatic or hydraulic pressure. In some instances, the cylinders 106a, b may be coupled to a surgical console that includes a pneumatic system. The pneumatics system may apply a positive pressure on the piston 112a or 112b of cylinder 106a or 106b, respectively, to cause a displacement of the piston 112a or 112b in the direction of arrow 122. This movement of piston 112a or 112b of cylinder 106a or 106b, respectively, applies pressure to and the displacement of the hydraulic fluid 114a, b, respectively. The hydraulic fluid 114a, b, consequently, displaces pistons 112b, d of cylinders 108a, b, respectively. In some implementations, the actuators 118a, b and cylinders 106a, b may form a pump actuator 119.

To displace the piston 112a in the direction of arrow 124, a vacuum may be applied to the piston 112a. As a result, the vacuum displaces the piston 112a of cylinder 106a, the hydraulic fluid 114a, and piston 112b of cylinder 108a in the direction of arrow 124. Similarly, a vacuum applied to piston 112c displaces piston 112c of the cylinder 106b, the hydraulic fluid 114b, and the piston 112d of cylinder 108b in the direction of arrow 124. Thus, pneumatics may be utilized to operate the first fluid circuit 102 and the second fluid circuit 104. Hydraulics may be used in a similar way to actuate the pistons 112a, c in cylinders 106a, b, respectively.

In some implementations, the cylinders 108a, b may be incorporated into a hand piece 126. For example, the system 100 may be selectively coupled and decoupled to the hand piece 126. Particularly, in some implementations, at least a portion of system 100 may be attachable to or received inside of a housing of a surgical hand piece. For example, in some instances, a portion of the system 100, such as all or a portion of the cylinders 108a, b, may be received into a cavity formed in hand piece 126. Thus, in such instances, cylinders 108a, b become an integrated part of the hand piece 126. An integral connection may further reduce a length of aspiration line between a surgical site and the system 100, resulting in a more responsive aspiration process. In still other instances, a conduit in communication with aspiration conduit 128 may extend between the system 100 and a hand piece.

Figure 5:
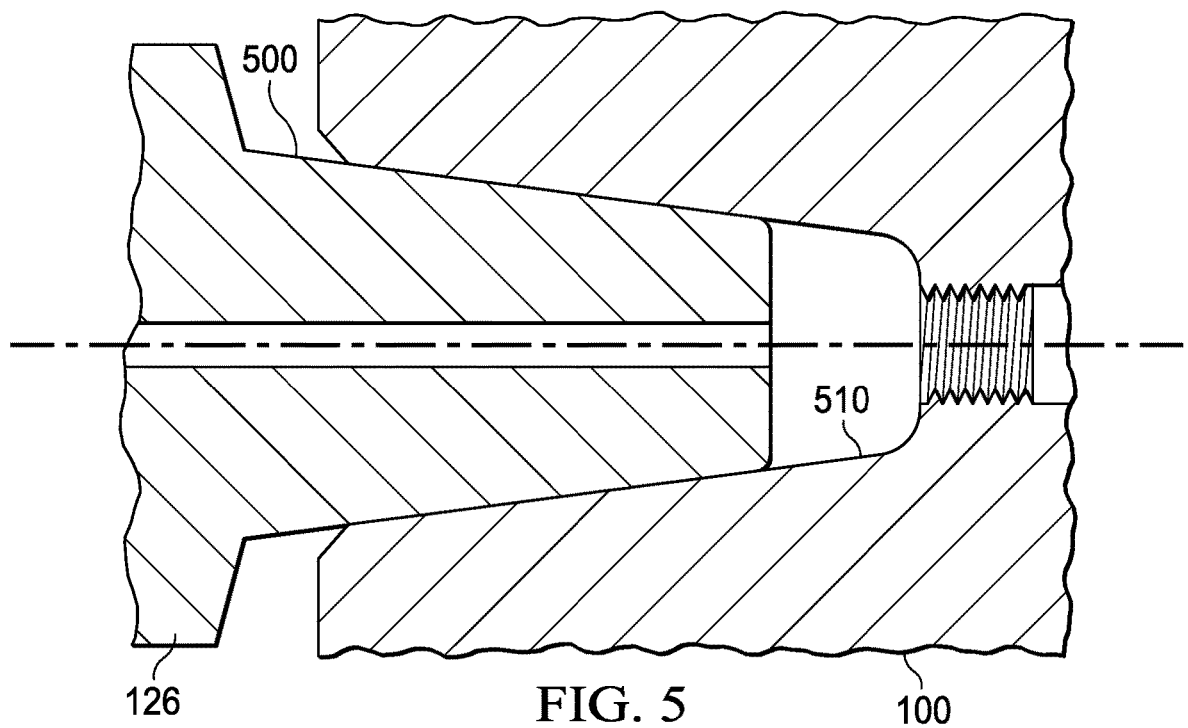
FIGS. 5 and 6 show example connections between an example hydraulic pump and an example hand piece.

For example, in some instances, the system 100 and the hand piece 126 may be coupled with a luer connection, as illustrated in FIG. 5. Particularly, FIG. 5 shows a portion of the hand piece 126 forming a male luer 500. A portion of the system 100 is also illustrated. The system 100 includes a receptacle 510. The receptacle 510 receives the male luer 500 to connect the system 100 with the hand piece 126.

Figure 6:
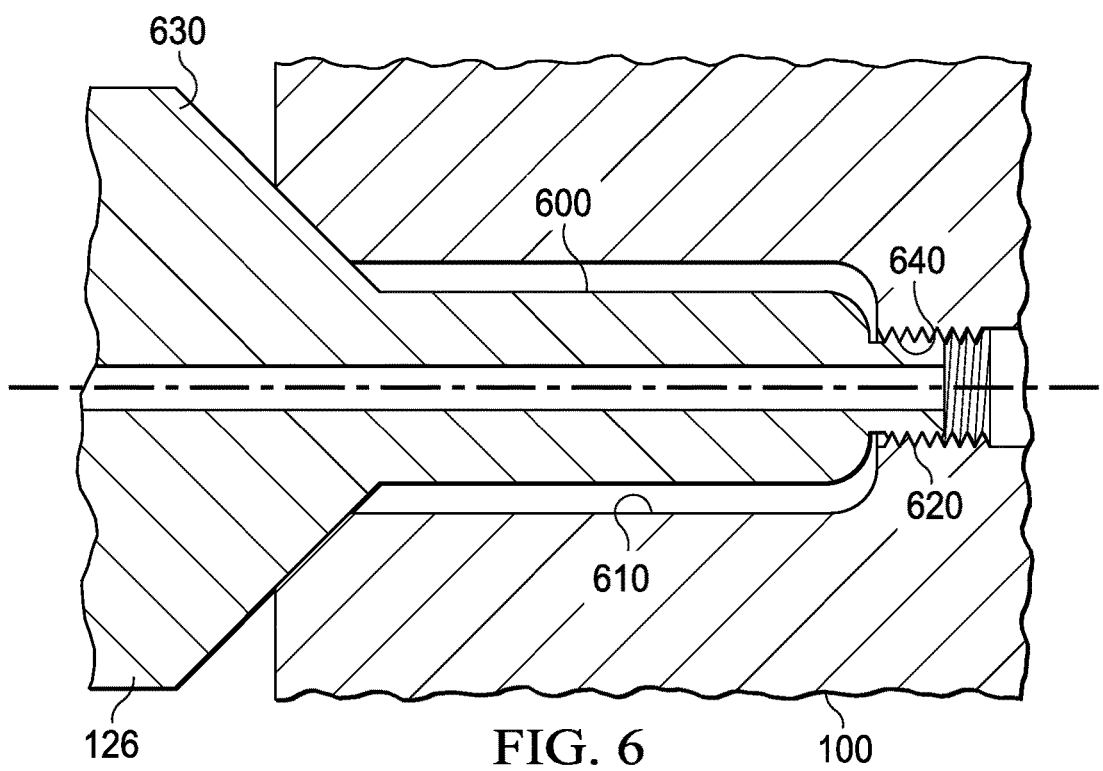

In other instances, the connection between the system 100 and the hand piece 126 may also include a threaded connection. FIG. 6. shows another example connection between hand piece 126 and system 100. Particularly, the hand piece 126 may include a male luer 600 that includes a distal external thread 620 and a tapered portion 630. The distal external thread 620 correspondingly engages an internal thread 640 formed on an internal surface of receptacle 610. The tapered portion 630 engages a chamfer 650 to align the hand piece 126 and system 100 as well as to form a rigid attachment and seal therebteween.

The ability to selectively couple and decouple the hand piece 126 and system 100 may be particularly advantageous in those instances where the system 100 is a disposable system. Thus, in some instances, the system 100 may be disposable after a single use. In other instances, the system 100 may be reusable and still selectively coupleable and decoupleable to the hand piece 126. In some instance, the hand piece 126 may be an ophthalmic surgical hand piece. In some instances, the hand piece 126 may be a phacoemulsification hand piece. In still other instances, the hand piece 126 may be a hand piece operable to provide both irrigation and aspiration functionality. Other types of hand pieces may also be coupleable to the pump systems disclosed herein and are, therefore, within the scope of this disclosure.

The cylinders 106 may be coupled to or provided in a surgical console. For example cylinders 106 may be received into receptacles formed in the surgical console. In other instances, the cylinders 106 may be coupled to fittings provided on a surgical console. However, in some instances, the cylinders 106 may be coupled to or otherwise received into a surgical console in any suitable way.

The system 100 may also include an aspiration line 128. The aspiration line 128 may include a cannula or needle that may be introduced into a working area within a body. A distal end 130 of the aspiration line 128 may include an aperture through which an aspiration flow may enter the aspiration line from the working area. The aspiration line 128 may also include a length of aspiration conduit within the hand piece 126.

In the example shown, the aspiration line 128 divides into aspiration line 132 that provides fluid communication with the cylinder 108 of the first fluid circuit 102, and aspiration line 134 that provides fluid communication with cylinder 108 of the second fluid circuit 104. A distance defined by aspiration line 132 or aspiration line 134 may be short. A minimal distance defined by aspiration lines 132 and 134 reduces a post occlusion surge (i.e., a surge of fluid and associated pressure drop in the eye due to the passage of an occlusion within an aspiration line). In some implementations, a length of the aspiration lines 132 and 134 are significantly shorter than an overall length of conventional tubing extending form a surgical console to a hand piece. Thus, the system 100 responds much more quickly to a post occlusion surge and substantially reduces risks to a patient associated with a post occlusion surge. In some implementations, a length of the aspiration line 132 and/or 134 may be less than two feet. In other instances, the length of the aspiration line 132 and/or 134 may be less than one foot. In other instances, the length of the aspiration line 132 and/or 134 may be less than six inches. In still other implementations, the length of aspiration line 132 and/or 134 may be only two to three centimeters or less. A short distance between the distal end 130 of the aspiration line 128 and the cylinders 108 results in improved fluidic stability.

Although FIG. 1 shows a single aspiration line extending to the cylinders 108a and 108b, i.e., aspiration lines 132, 134, it other implementations, a plurality of aspiration lines may extend to each of the cylinders 108a and 108b.

Aspiration fluid traveling through the aspiration line 132 and the aspiration line 134 enters the cylinders 108a and 108b of the respective fluid circuits 102, 104 through inlet 136 and inlet 138, respectively. A one-way valve 140 may be disposed in the aspiration line 136, and a one-way valve 142 may be disposed in aspiration line 134. One-way valves described herein may be any type of valve operable to permit passage of a fluid in one direction but prevent passage of fluid in the opposite direction. Example one-way valves include a ball-type check valve or a flap valve.

Each of the cylinders 108a and 108b may also include a respective outlet 144 and outlet 146. An aspiration conduit 148 and aspiration conduit 150 extend from the respective outlets 144, 146. A one-way valve 152 may be disposed in the aspiration line 148, and one-way valve 154 may be disposed in aspiration line 150. The aspiration conduit 148 and aspiration conduit 150 fluidly communicate with aspiration conduit 156 at a union 158. The aspiration conduit 156 extends to an aspiration collection container 160. In some implementations, the collection chamber 160 may be a bag or some other type of container for holding fluid and materials that has been aspirated from the patient's eye. In other implementations, the drainage chamber 160 may be a waste drain. In some instances, the cylinders 108, the one-way valves 140, 142, 152, and 154, and the aspiration lines 132, 134, 148, 150, and 156 may be referred to as aspiration pump 155.

In operation, the actuators 118a, b are moved into the engaged configuration to engage the connecting members 116a, b, respectively. One of the actuators 118a, b then may be moved in the direction of arrow 124 and the other actuator 118a, b may be moved in the direction of arrow 122. When moved in the direction of arrow 124, the piston 112a or piston 112c in cylinder 106a or cylinder 106b displaces the piston 112b or 112d, respectively, in the associated cylinder 108a or 108b as described above.

Movement of the piston 112b or piston 112d in cylinder 108a or cylinder 108b, respectively, in the direction of arrow 124 generates a vacuum in the respective cylinder 108a or 108b, causing fluid to enter the aperture formed in the distal end 130 of the aspiration line 128 and to be conducted therethrough. For example, in the illustrated example of FIG. 1, if the piston 112b of cylinder 108a of the first fluid circuit 102 is moved in the direction of arrow 124, the generated aspiration fluid flow is conducted through the aspiration line 128 and into aspiration line 132. The aspiration fluid flow passes through one-way valve 140 and into the interior of cylinder 108a. If the second fluid circuit 104 is not being actuated such that piston 112d of cylinder 108b is not being displaced in the direction of arrow 124, the aspiration fluid flow will not flow through aspiration line 134. Also, because valve 152 is a one-way valve, any fluid contained in aspiration line 148 and 156 is prevented from entering the interior of cylinder 108a through these structures when the piston 112b moves in the direction of arrow 124.

When the actuator 118a associated with the first fluid circuit 102 reversed, the piston 112b of cylinder 108a is moved in the direction of arrow 122. The aspirated fluid contained within the interior of the cylinder 108a is pressurized and forced into the aspiration line 148, one-way valve 152, and aspiration line 156. This aspirated fluid is ultimately conveyed to collection container 160 as pumping continues. Again, because valve 140 is a one-way valve, the aspirated fluid is prevented from traveling back through the valve 140 and aspiration lines 132 and 128.

In some implementations, the collection container 160 may be disposed a small distance from the hand piece 126 as opposed to being disposed in a surgical console. As a result, the aspirated material need not be pumped a large distance from the hand piece. In some instances, aspiration lines 148 and 150 may remain separate from each other and be separately coupled the collection container 160.

In some implementations, as the piston 112b of the first fluid circuit 102 or the piston 112d of the second fluid circuit 104 is moved in one of the directions corresponding to arrows 122 and 124, the piston 112b or piston 112d of the other of the first fluid circuit 102 or fluid circuit 104, respectively, may be moved in the opposite direction. Thus, during the times the pistons 112b, d are moving, a continuous fluid flow through the aspiration lines 128 and 256 occurs.

In some implementations, pulsations or variations in the aspiration fluid flow rate may be substantially reduced or eliminated by operation of pistons 112a, b of the first fluid circuit 102 and pistons 112c, d of the second fluid circuit 104 out of phase from each other. In these instances, the pistons 112a, b in first fluid circuit 102 are considered to be out of phase with the pistons 112c, d of the second fluid circuit 104 because the pistons 112a, b of the first fluid circuit 102 do not reach the end of their stroke in either of the directions of arrows 122 and 124 at the same time that the pistons 112c, d of the second fluid circuit 104 reach the end of their stroke in the either of the directions of arrow 122 and 124.

Figure 2:
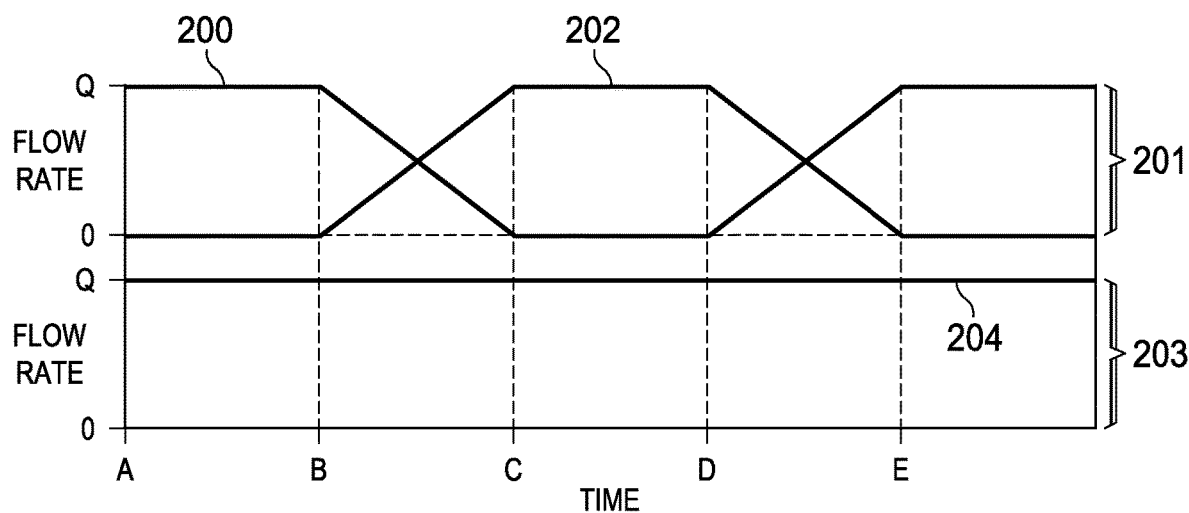
FIG. 2 shows flow rate graphs for individual fluid circuits and an overall flow rate of a pump system as a whole.

For example, FIG. 2 shows flow rate graphs for individual fluid circuits in a first portion 201 and an overall flow rate of a pump system as a whole in a second portion 203. Flow rate 200 and flow rate 202 are shown in the first portion 201. Flow rate 200 reflects an aspiration fluid flow rate over time for a first fluid circuit of a pump system. For example, such a pump system may be similar to system 100. Thus, flow rate 200 may reflect changes in an aspiration fluid flow rate associated with fluid being drawn into cylinder 108a of the first fluid circuit 102. Similarly, flow rate 202 reflects changes to an aspiration fluid flow rate over time for another fluid circuit of a pump system. For example, flow rate 202 may reflect changes over time of an aspiration fluid flow being drawn into cylinder 108b of second fluid circuit 104. Flow rate 204 shown in the second portion 203 represents the total aspiration flow rate for an entire system. Thus, for example, flow rate 204 may reflect changes over time to an aspiration fluid flow rate produced by system 100. While the system 100, first fluid circuit 102, and second fluid circuit 104 are provided as examples, the flow rate performance illustrated in the example shown in FIG. 2 may be applicable to any of the systems described herein or otherwise encompassed by the present disclosure.

Referring to the first portion 201 of FIG. 2, at time A, flow rate 200 is at a level of Q and flow rate 202 is zero. At time B, flow rate 200 begins to decrease while flow rate 202 begins to increase. The decrease in flow rate 200 may be the result of a piston approaching a limit of its stroke. For example, in the context system 100, the decrease in flow rate from time B to time C may be the result of piston 112b of cylinder 108a of the first fluid circuit 102 approaching its stroke limit in the direction of arrow 124.

Similarly, the increase in flow rate from time B to time C for flow rate 202 may be the result of piston 112d of cylinder 108b of the second fluid circuit 104 beginning its stroke in the direction of arrow 124. At time C, the flow rate 200 is zero, and the flow rate 202 is Q. For any time between times B and C, the combined flow rate of flow rate 200 and flow rate 202 is equal to Q, because, for a given reduction in flow rate 200, flow rate 202 is increasing an equal amount. Thus, the combined flow rate is Q. This combined flow rate of flow rates 200, 202 is illustrated as flow rate 204. The zero flow rate for flow rates 200 and 202 may be understood as the time during which the cylinders 108 are pushing aspirated fluid therein out toward collection container 160.

As illustrated by FIG. 2, to provide a continuous aspiration fluid flow, the movement of pistons 112a, b in the first fluid circuit 102 and the pistons 112c, d in the second fluid circuit 104 are out of phase. When pistons 112a, b of the first fluid circuit 102 are slowing as they reach the end of their stroke in the direction of arrow 124, the pistons 112c, d in the second fluid circuit 104 are beginning to move in the direction of arrow 124 to draw aspiration into cylinder 108a. Consequently, the pistons 112c, d of the second fluid circuit 104 reach the end of their stroke in the direction of arrow 122 at time B and begin moving in the same direction as the pistons 112a, b in the first fluid circuit 102 from time B until time C. Thus, during the time period between times B and C, the pistons 112a, b of the first fluid circuit 102 and the pistons 112c, d of the second fluid circuit 104 are moving in the same direction, i.e., in the direction of arrow 124. Similarly, during the time period between times D and E, the pistons 112a, b and pistons 112c, d are also moving in the direction of arrow 124. The out of phase movement of the pistons 112a, b in the first fluid circuit 102 and the pistons 112c, d in the second fluid circuit 104 provide for a continuous aspiration flow, as illustrated by the flow rate 204 in FIG. 2, thereby eliminating or substantially reducing any fluctuations or pulsations in the aspiration fluid flow. This periodic movement of the pistons 112a, b within the first fluid circuit 102 and pistons 112c, d in the second fluid circuit 104 may continue for any desired length of time.

A controller may be used to operate the first fluid circuit 102 and the second fluid circuit 104. For example, in some instances, a controller within a surgical console to which the system 100 is coupled may be used to operate the first and second fluid circuits 102 and 104 out of phase as described above. The controller, though, may be utilized or programmed to operate the first fluid circuit 102 and the second fluid circuit 104 in any desired manner with respect to each other. In some implementations, the controller may control actuators 118a, b. For example, the controller may be utilized to control the stroke of the actuators 118a, b and the movement of the actuators 118a, b relative to each other. The controller may also be used to control movement of the grasping members 120 between the engaged configuration and the disengaged configuration.

Another advantage of the system 100 is that the system 100 response rapidly to inputs made to the system 100 by the actuators 118a, b. Because liquids are essentially incompressible, an input to the pistons 112a, c in the cylinders 106a, b, respectively, results in essentially an instantaneous reaction of the corresponding pistons 112b, d in the cylinders 108a, b, respectively. This rapid response may also be desirable in the context of cessation of pumping. For example, the system 100 may be used to aspirate an emulsified lens from an eye. During aspiration of the emulsified lens, lens particles may cause an occlusion within one or more of the aspiration lines. Once the occlusion is removed, a rapid pressure decrease within the eye may result as fluid is quickly aspirated therefrom. This rapid evacuation of fluid from the eye can cause damage, including, for example, "shallowing" of the eye. For example, during a phacoemulsification procedure, shallowing due to a decrease in the pressure within the anterior segment of the eye can cause the back of the capsular bag to be drawn towards a phacoemulsification tip. Contact with the phacoemulsification tip may rupture the back of the capsular bag. Therefore, rapid response to fluctuations in aspiration fluid flow can reduce the risk of injury to patients.

The system 100 is operable to quickly respond to a change in IOP. For example, if a decrease in IOP, for example a decrease in IOP below a selected pressure, the actuators 118a, b may be quickly moved into their disengaged configuration, immediately stopping the pumping action of system 100. This immediate responsiveness of the system 100 is, in large part, the result of the incompressible nature of the hydraulic fluid 114a, b.

The rapid responsiveness of the system 100 may also be realized in other implementations utilizing other ways of cycling the first and second fluid circuits 102 and 104. Examples of these alternatives are described above, such as by pneumatic or hydraulic actuation.

Another benefit of the system 100 is that the system does not require an electric motor or other electrical device at the hand piece 126 to power the system 100. Consequently, the hand piece 126 has less weight and complexity and reduces the size of the hand piece 126. Further, the hand piece avoids the need for additional power, thereby avoiding a secondary electrical cable extending to the hand piece 126. This, too, reduces the weight and improves a user's ability to manipulate the hand piece 126. Still further, the system 100 may be disposable after a single use. This provides convenience to the user and eliminates the need to sterilize the system 100. Further, the system 100 may be operably interchangeable with different types of hand pieces. That is, a single type of system may be coupled to and operate different types of hand pieces.

In some implementations, the system 100 may be prefilled prior to being supplied to a user. Thus, a user is capable of selecting a system 100 and immediately coupling the system 100 to a hand piece for use. In other implementations, the system 100 may be filled with hydraulic fluid 114a, b, also referred to as "primed," immediately prior to use. In some instances, the hydraulic fluid 114a, b may be a liquid. For example, in some instances, the hydraulic fluid 114a, b may be a balanced salt solution, such as BSS® Sterile Irrigation Solution produced by Alcon Laboratories, Inc. of Fort Worth Tex. Thus, in some instances, a liquid used to prime the system 100 may be a liquid used for other purposes during a surgical procedure. In still other implementations, any suitable liquid may be used to prime the system 100.

In some implementations, the pistons 112a, c in cylinders 106a, b may be the same size as the pistons 112b, d in cylinders 108a, b. In other implementations, the size of the pistons 112a, c in the cylinders 106a, b may be different than the size of the pistons 112b, d in cylinders 108a, b. For example, in some instances, the size of the piston 112a, c in cylinder 106a, b may be larger than a size of the piston 112b, d in cylinder 108a, b. In other instances, the size of piston 112a, c in cylinder 106a, b may be smaller than a size of piston 112b, d in cylinder 108a, b.

In still other implementations, the system 100 may include additional fluid circuits. That is, in some implementations, the system 100 may more than two fluid circuits. In still other implementations, example systems may include a single fluid circuit.

Figure 3:
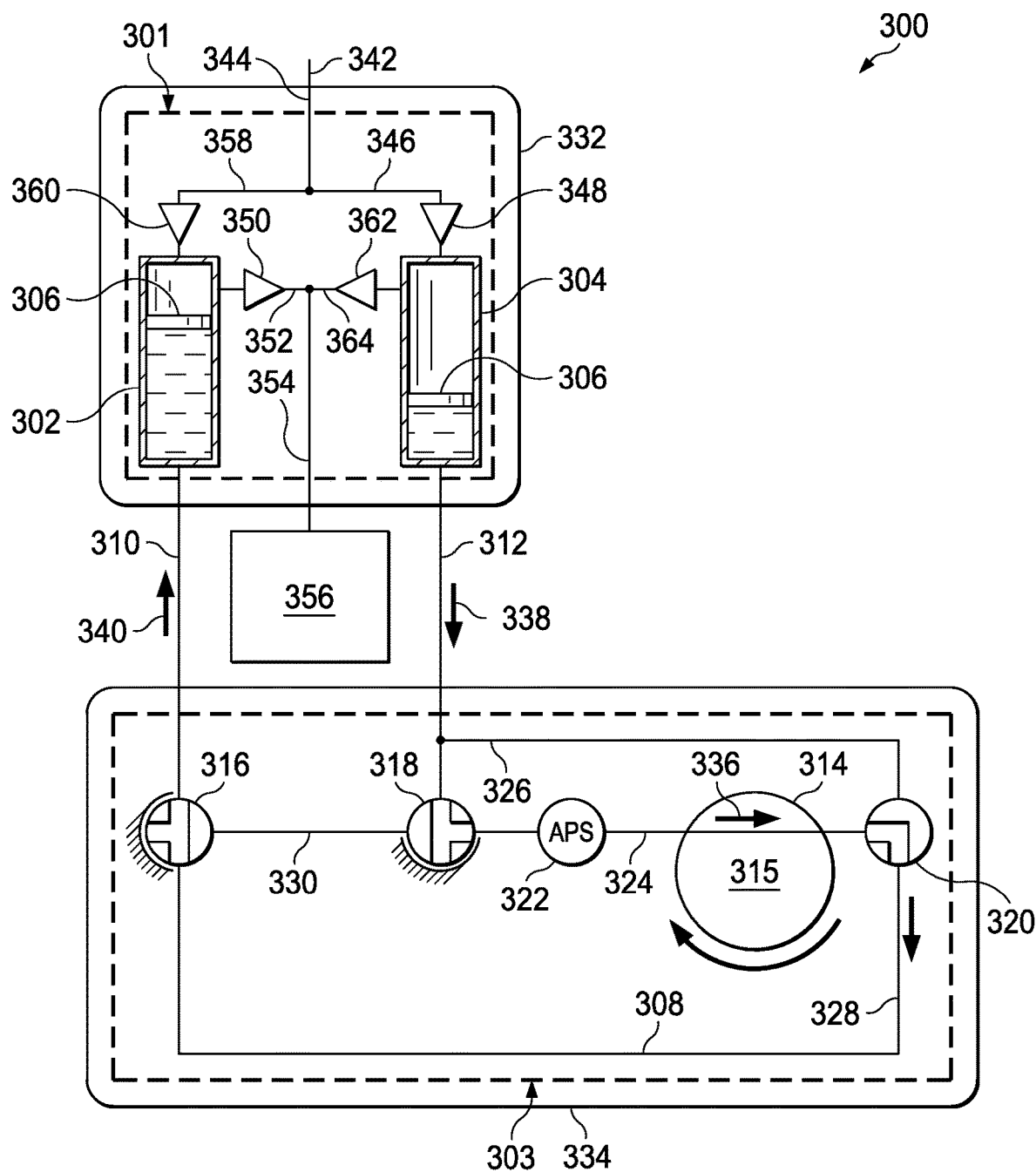
FIGS. 3 and 4 show schematic illustrations of another example hydraulic pump.
Figure 4:
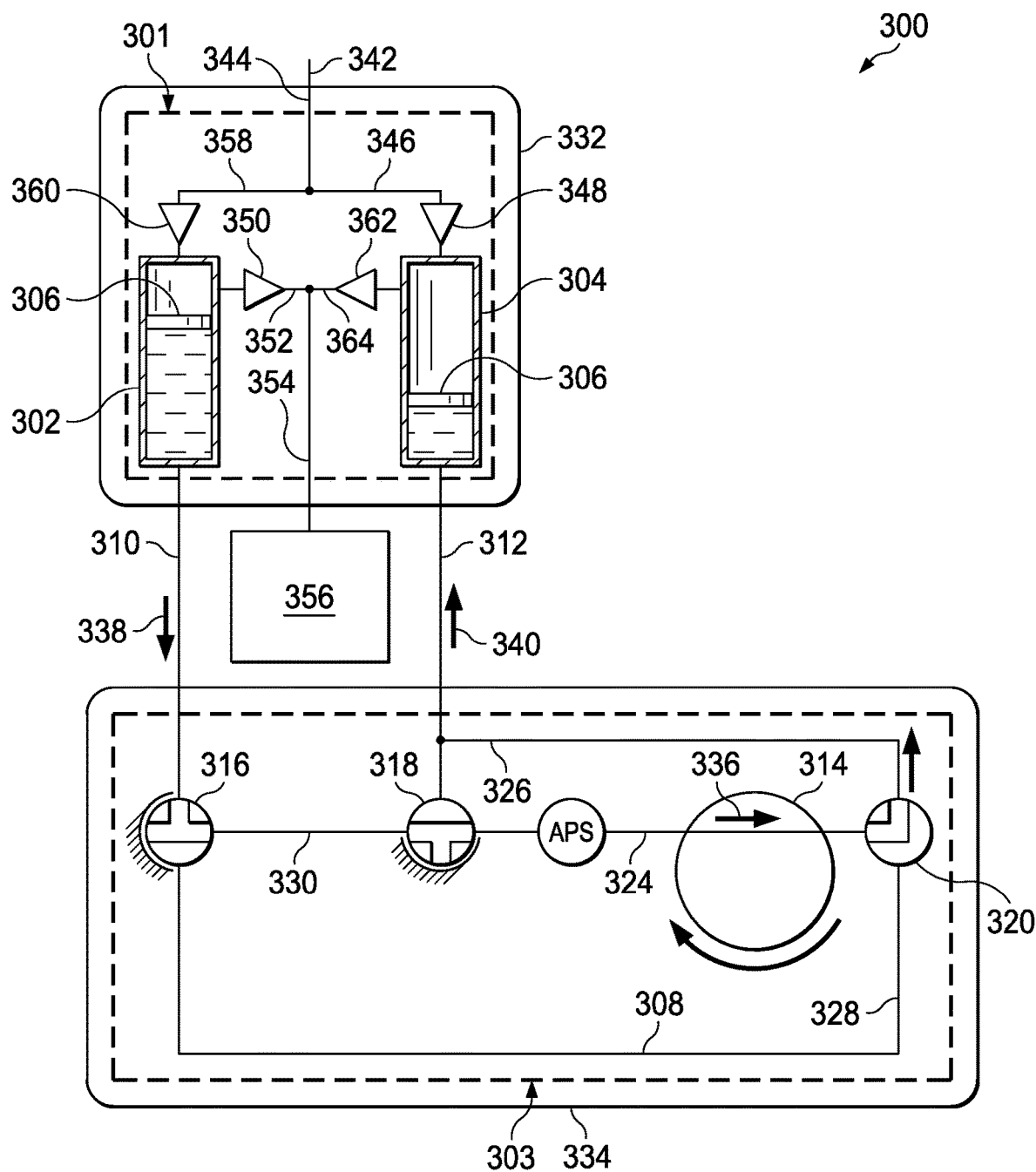

FIGS. 3 and 4 illustrate another example pump system 300. System 300 may be similar to system 100, except that system 300 does not include the actuators 118 and cylinders 106. System 300 includes an aspiration pump 301 and a pump actuator 303.

The aspiration pump 301 includes a first cylinder 302 and a second cylinder 304. Each of the first cylinder 302 and the second cylinder 304 include a piston 306 moveable therein. The pump actuator 303 includes a fluid conduit network 308. Interiors of the first and second cylinders 302, 304 are in fluid communication with a fluid conduit network 308 via fluid conduits 310 and 312. Particularly, fluid conduit 310 fluidly communicates with an interior of the first cylinder 302, and fluid conduit 312 fluidly communicates with an interior of the second cylinder 304.

The pump actuator 303 may also include a pump 314; a plurality of rotary valves 316, 318, and 320; and an aspiration pressure sensor 322. The aspiration pressure sensor 322 is disposed in a fluid conduit 324 and is operative to detect a pressure within the fluid conduit network 308 and, particularly, in fluid conduit 324. The pressure sensed by the pressure sensor 322 may be correlated to reflect a pressure of the aspiration fluid flow. The fluid conduit 324 extends between rotary valve 318 and rotary valve 320. Rotary valve 316 provides selective fluid communication between fluid conduit 310 and fluid conduit 328 in a first position and fluid communication between fluid conduit 330 and fluid conduit 310 in a second position. Rotary valve 318 provides selective fluid communication between fluid conduit 324 and fluid conduit 312 in a first position and fluid communication between fluid conduit 330 and fluid conduit 324 in a second position. Rotary valve 320 provides selective fluid communication between fluid conduit 324 and fluid conduit 328 in a first position and fluid communication between fluid conduit 324 and fluid conduit 326 in a second position.

In some implementations, the pump 314 may be a peristaltic pump. For example, pump 314 may include a rotatable head 315 that is adapted to engage a flexible portion of fluid conduit 324 to generate a peristaltic fluid flow. In some instances, the head 315 may include a plurality of protrusions, such as a plurality of rollers, adapted to engage a flexible conduit to generate a peristaltic fluid flow. For example, a portion of fluid conduit 324 may be formed of a flexible material that is deformable by the head 315. Thus, in some instances, the head 315 of the pump 326 may engage and compress the flexible portion of fluid conduit 324 to generate a fluid flow. However, a peristaltic pump is provided merely as an example and the scope of the disclosure is not so limited. Rather, the pump 314 may be any desired or suitable pump.

In some implementations, the pump actuator 330 of the system 300 may be receivable into a cassette receiving portion of a surgical console. In such implementations, the pump head 315 may be a part of the surgical console. As explained above, the pump head 315 may be operable to engage a portion of a fluid conduit of the fluid conduit network 308, such as a flexible portion of the fluid conduit 324. In some instances, the portion of fluid conduit network 324 may be arc-shaped. Consequently, the system 300 may be a single, integrated system that may be quickly coupled and decoupled to a hand piece, such as hand piece 332, and a cassette receiving portion of a surgical console, such as surgical console 334. For example, in some implementations, the aspiration pump 301 may be attached to a housing of hand piece 332. In some implementations, at least a portion of the aspiration pump 301 may be received within a housing of hand piece 332. In some instances, the aspiration pump 301 and hand piece 332 may be connected in a manner such as one of the manners similar to those shown in FIGS. 5 and 6. Thus, in some instances, aspiration pump 301 may be integral with the hand piece 332. In some instances, the aspiration pump 301 may be attached to hand piece 332 such that fluid conduits 310 and 312 extend from the hand piece 332. Thus, the system 300 may be quickly implemented prior to a surgical procedure. Further, in some instances, the system 300 may be disposable after a single use. In some instances, the system 300 may be pre-filled with a liquid circulated within the fluid conduit network 308. In other instances, the system 300 may be primed with a liquid just prior to use. A liquid, such as BSS® Sterile Irrigation Solution produced by Alcon Laboratories, Inc. of Fort Worth Tex., may be used in system 300. However, the scope of the disclosure is not so limited. Rather, any suitable liquid may be used.

During operation, the pump 314 may be operable to pump fluid in a single direction. For example, as shown in FIG. 3, the pump 314 is operable to pump fluid in the direction of arrow 336. With rotary valves 316, 318, and 320 in their respective first position, shown in FIG. 3, the pump 314 is operable to pump fluid from the interior of the cylinder 304, through fluid conduits 312, 324, 328, 310, and into the interior of cylinder 306. As a result, the piston 306 in cylinder 304 is displaced in the direction of arrow 338, and piston 306 of cylinder 302 is displaced in the direction of arrow 340.

System 300 includes an arrangement of aspiration lines similar to system 100 to aspirate materials. As piston 306 of cylinder 304 is displaced in the direction of arrow 306, material is aspirated into a distal end 342 of aspiration line 344, through aspiration line 346, through one-way valve 348, and into the interior of cylinder 304. As piston 302 is displaced in the direction of arrow 340, aspirated material present in the cylinder 306 is forced through one-way valve 350, aspiration line 352, aspiration line 354, and into a collection container 356.

FIG. 4 shows system 300 in which rotary valves 316, 318, and 320 are in their respective second positions. As the pump 314 continues to pump fluid in the direction of arrow 336, the fluid flows from the interior of cylinder 302; through fluid conduits 330, 324, 326, and 312; and enters the interior of cylinder 304. The fluid movement results in displacement of the piston 306 of cylinder 302 in the direction of arrow 338 and the displacement of the piston 306 of cylinder 304 in the direction of arrow 340. Consequently, aspirated material is drawn into the distal end 342 of the aspiration line 344, through aspiration line 344, aspiration line 358, one-way valve 360, and into cylinder 302. Simultaneously, aspirated material within cylinder 304 is pushed through one-way valve 362, through aspiration lines 364 and 354, and into collection container 356.

The positions of the rotary valves 316, 318, and 320 as well as the operation of the pump 314 (e.g., the fluid pumping direction and pumping speed) may also be controlled by a controller. Further, by manipulation of the rotary valves 316, 318, and 320 between their respective first and second positions causes a reversal in the movement of the pistons 306 in their respective cylinders. That is, the pump actuator 303 is operable to oscillate the pistons 306 within their respective cylinders.

Additionally, in some implementations, the pumping action of the pistons 306 within the cylinders 302 and 304 may be out of phase in a manner similar to that described above and as illustrated in FIG. 2. As a result, the system 300 is operable to generate a constant aspiration flow rate with elimination or the substantial reduction in any pulsations or fluctuations in aspiration fluid flow. Although an example pump actuator 303 is shown, the scope of the disclosure is not so limited. Rather, for example, the number and type of rotary valves may be varied and/or the arrangement of the fluid conduits in the fluid conduit network may be varied.

Figure 8:
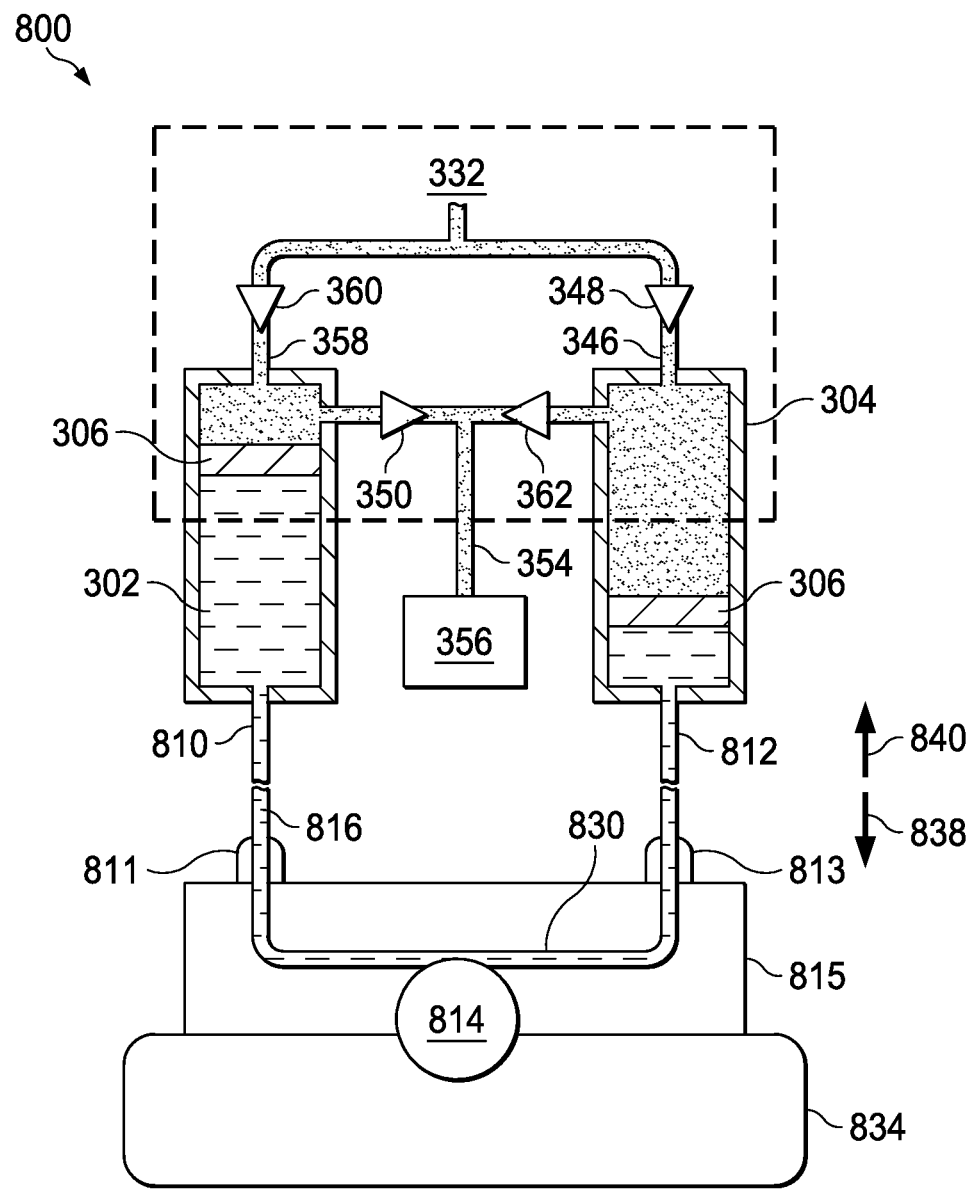
FIG. 8 is a flowchart showing an example method for pumping using a hydraulic pump.

FIG. 8 shows another example pump system 800. System 800 may be similar to system 300 shown in FIGS. 3 and 4. However, in system 800, conduits 810 and 812 are in fluid communication with each other. A pump 814 is operable to generate a fluid flow through the conduits 810 and 812. In some implementations, the conduits 810 and 812 connect with or otherwise form a part of a cassette attached to a surgical console 834. In some instances, the conduits 810 and 812 attach to respective ports 811 and 813 of cassette 815. A conduit 830 may extend between the two ports 811 and 813 and fluidly communicate with conduits 810 and 812. In some implementations, conduits 810, 812, and 830 may be a continuous length of flexible tubing.

Similar to pump 314, the pump 814 may be a positive displacement peristaltic pump used to pump fluids contained within a flexible tube disposed adjacent a pump rotor. The pump 814 includes a rotatable head. The rotatable head includes a number of protrusions adapted to engage and compress conduit 830. These protrusions compress a portion of the conduit 830 adjacent the rotatable head. As the rotatable head turns, the portion of the conduit 330 under compression by the protrusions is pinched closed, thus forcing the fluid through the tube.

As the pump 814 rotates the rotatable head in a clockwise direction, hydraulic fluid 816 may be moved from the conduit 810 and into conduit 812. Flow of the hydraulic fluid 816 in this direction results in movement of the piston 306 of cylinder 302 in the direction of arrow 838 and movement of piston 306 of cylinder 304 in the direction of arrow 840. Conversely, as the pump 814 rotates the rotatable head in a counterclockwise direction, hydraulic fluid 816 is moved moves in the opposite direction, causing piston 306 in cylinder 302 to move in the direction of arrow 840 and piston 306 in cylinder 304 to move in the direction of arrow 838. During operation of system 800, the pump 814 may alternatingly move in a clockwise and counter-clockwise direction, thus moving hydraulic fluid back and forth between the cylinders 302 and 304 in a reciprocating fashion. In some implementations, the console 834 may include two peristaltic pumps, each associated with a different one of the ports 811, 813. Both peristaltic pumps may be configured to move fluid in and out of the respective cylinders 302 and 304 in a reciprocating manner.

Figure 9:
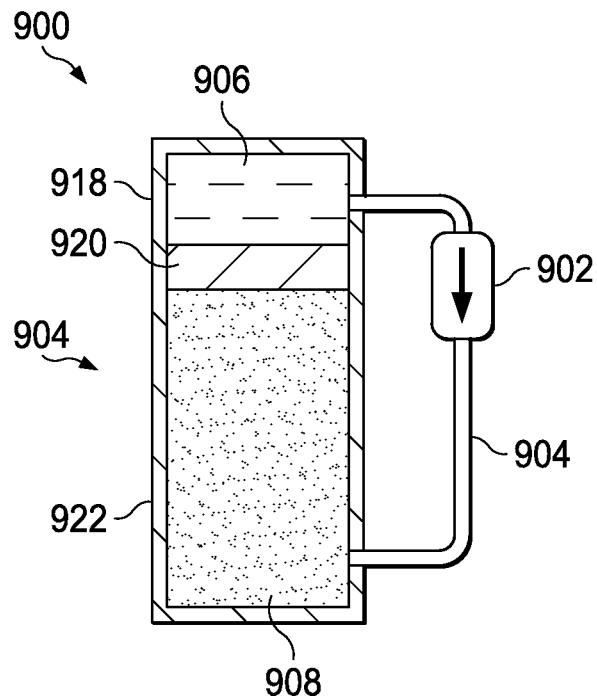
FIG. 9 illustrates an example pumping assembly.

FIG. 9 shows a pumping assembly 900 that may be engaged with the hand piece, such as hand piece 332 or hand piece 732, and may form a part of a pump system, such as any of the pump systems described herein. A priming connection 904 is disposed between the first portion 918 of cylinder 904 and a second portion 922 of the cylinder 904. Cylinder 904 may be similar to cylinders 108, 302, or 304. This priming connection 904 is operable to allow fluid to flow between the first portion 918 and the second portion 922 through a valve 902.

The valve 902 may be opened during the priming process, which occurs when preparing a pump system, such as any of the pump systems described herein, for surgery. In some implementations, a fluid 906 in the first portion 918 may be an irrigation fluid that is to be used during the course of the surgical procedure. Because priming the pump systems occurs before the surgical procedure, the fluid 906 is still clean as it has not been aspirated from a patient. After being transferred to the second portion 922, the fluid is used as the hydraulic fluid 908 for the pump system.

In some implementations, the second portions 922 of the cylinder 904 may be filled with any suitable hydraulic fluid from any suitable source. For example, a saline solution for irrigation (such as a balanced salt solution) may be used as the hydraulic fluid. For example, a surgical console, such as any of the surgical consoles described here, may include a hydraulic fluid chamber that can store hydraulic fluid and fill the pump systems described herein as desired. Additionally, the pump systems may be stored with both of the second portion 922 of the cylinder 904 in a vacuum. In some implementations, the second portion 922 may include a vent that allows for the air to be purged before filling with fluid. The valve 902 may be opened to fill the second portion 922 as well as remainder of the pump system that utilizes the hydraulic fluid.

Figure 10:
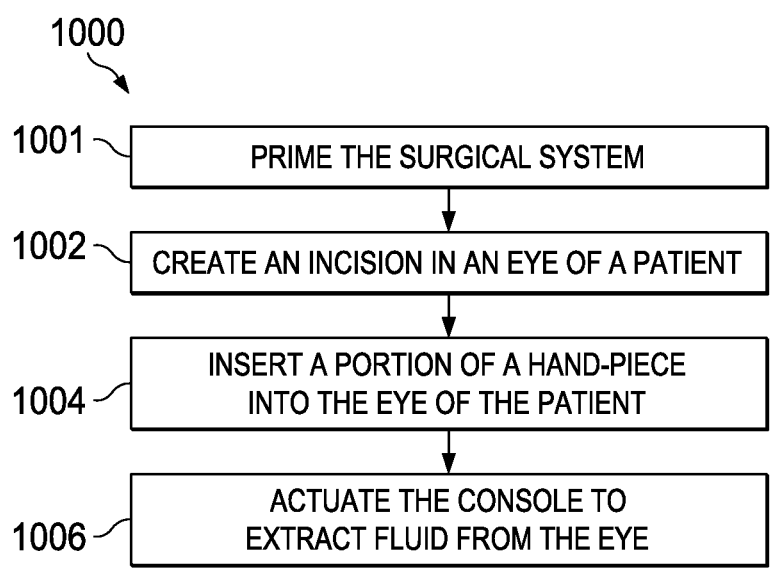
FIG. 10 is a flowchart of an example method for using a pump system for an ophthalmic surgical system.

FIG. 10 is a flowchart showing an illustrative method for using a pump system for an ophthalmic surgical system, such as, for example, surgical system 700. The pump system may include, for example, any of the pump systems 100, 300, and 800. According to the present example, at a step 1001, the surgical system is primed. The priming process includes getting the surgical system ready for a surgical procedure. This process may involve adding hydraulic fluid to the pump system. In some instances, the hydraulic fluid may be added using a priming connection, such as priming connection 904 as described above.

At a step 1002, the method 1000 includes creating an incision in an eye of a patient. At a step 1004, the method 1000 includes inserting a portion of a hand piece into the eye of the patient. Example hand pieces include any of the hand pieces described herein. For example, the hand piece may be a phacoemulsification hand piece, an irrigation and aspiration hand piece, or a hand piece that provides only aspiration. In some aspects, the portion inserted into the eye may be a hollow needle forming the instrument tip, such as, for example, instrument tip 725 shown in FIG. 7.

At step 1006, the method 1000 further includes actuating the pump system to extract fluid from the patient's eye. In some implementations, a connecting member, such as connecting member 116, is connected to a piston, such as piston 112. An actuator, such as actuator 118, included in the surgical console operates the pumping system to generate an aspiration fluid flow. Alternately, a pump and fluid conduit network, such as pump 314 and fluid conduit network 308, may be provided to generate an aspiration fluid flow.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. A surgical handpiece, comprising:
a first cylinder comprising:
   a first piston moveable therein, the first cylinder divided into a first portion and a second portion by the first piston;
   a first opening formed at a first end of the first cylinder; and
   a second opening formed at the first end of the first cylinder;
a second cylinder comprising:
   a second piston moveable therein, the second cylinder divided into a first portion and a second portion by the second piston;
   a third opening formed at a first end of the second cylinder; and
   a fourth opening formed at the first end of the second cylinder;
a first one-way valve in fluid communication with the first portion of the first cylinder via the first opening, fluid flowable through the first one-way valve into the first portion of the first cylinder when the first piston is displaced in a first direction;
a second one-way valve in fluid communication with the first portion of the first cylinder via the second opening, fluid flowable out of the first portion of the first cylinder through the second one-way valve when the first piston is displaced in a second direction opposite the first direction;
a third one-way valve in fluid communication with the first portion of the second cylinder via the third opening, fluid flowable through the third one-way valve into the first portion of the second cylinder when the second piston is displaced in the first direction;
a fourth one-way valve in fluid communication with the first portion of the second cylinder via the fourth opening, fluid flowable out of the first portion of the second cylinder through the fourth one-way valve when the second piston is displaced in the second direction; and
wherein the first piston and the second piston are configured to be displaced within their respective cylinders by a pump actuator located in a surgical console, the pump actuator comprising a pump, the pump comprising a rotatable head engaged with a flexible portion of a fluid pump conduit;
wherein the surgical handpiece is coupled to the surgical console and the pump actuator, wherein the pump actuator comprises:
   a fluid conduit network in communication with the second portion of the first cylinder and the second portion of the second cylinder;
   the pump in fluid communication with the fluid conduit network and adapted to pump fluid therethrough; and
   a plurality of valves disposed in the fluid conduit network, the plurality of valves moveable between a first position in which the first piston is displaced in the first direction and the second piston is displaced in the second direction and a second position in which the first piston is displaced in the second direction and the second piston is displaced in the first direction.

2. The surgical handpiece of claim 1, wherein the pump actuator is receivable into a cassette receiving portion of the surgical console.

* * * * *